United States Patent [19]
Zarkoob et al.

[11] Patent Number: 6,110,590
[45] Date of Patent: Aug. 29, 2000

[54] SYNTHETICALLY SPUN SILK NANOFIBERS AND A PROCESS FOR MAKING THE SAME

[75] Inventors: Shahrzad Zarkoob, Cuyahoga Falls; Darrell H. Reneker, Akron; Dale Ertley, Kent; R. K. Eby, Akron; Steven D. Hudson, Cleveland Heights, all of Ohio

[73] Assignee: The University of Akron, Akron, Ohio

[21] Appl. No.: 09/096,904

[22] Filed: Jun. 12, 1998

Related U.S. Application Data

[60] Provisional application No. 60/081,947, Apr. 15, 1998.

[51] Int. Cl.$^7$ .................................................. D02G 3/00
[52] U.S. Cl. .......................................... 428/364; 428/221
[58] Field of Search ................................. 442/221, 364; 530/353; 8/127.6

[56] References Cited

U.S. PATENT DOCUMENTS

| | | | |
|---|---|---|---|
| 5,171,505 | 12/1992 | Lock | 264/202 |
| 5,252,277 | 10/1993 | Uy | 264/129 |
| 5,252,285 | 10/1993 | Lock | 264/202 |
| 5,670,483 | 9/1997 | Zhang et al. | 530/324 |

OTHER PUBLICATIONS

"Spinning of Protein Polymer Fibers" by Cappello and McGrath, Silk Polymers: *Materials Science and Biotechnology*, pp. 311–327, Jul. 1993.

"Electrospinning Process and Applications of Electrospun Fibers" by Doshi and Reneker, reprint of *Journal of Electrostatics: Fundamentals, Applications and Hazards*, pp. 151–160, 1995.

"Nanometre Diameter Fibres of Polymer, Produced by Electrospinning" by Reneker and Chun, *Nanotechnology*, vol. 7, pp. 216–223, 1996.

"DNA Fibers by Electrospinning" by Fang and Reneker, *J. Macromol. Sci.–Phys.*, vol. B36(2), pp. 169–173, 1997.

"Structural and Morphological Investigations of Natural Silks" by Shahrzad Zarkoob, Research Presentation, Goodyear Auditorium, Polymer Science Building, Apr. 30, 1998.

"Comparative Structural Characterization of Naturally and Synthetically–Spun Fibers of Bombyx mori Fibroin" by Trabbic and Yager, *Macromolecules*, vol. 31, pp. 462–471, 1998.

"A Microfabricated Wet–Spinning Apparatus to Spin Fibers of Silk Proteins. Structure—Property Correlations" by Liivak et al., *Macromolecules*, vol. 31, pp. 2947–2951, 1998.

"Silk Fibroin/Cellulose Blend Films: Preparation, Structure, and Physical Properties" by Freddi et al., *J. of Applied Polymer Science*, vol. 56, pp. 1537–1545, 1995.

*Primary Examiner*—Newton Edwards
*Attorney, Agent, or Firm*—Renner, Kenner, Greive, Bobak, Taylor & Weber

[57] ABSTRACT

A silk nanofiber composite network produced by forming a solution of silk fiber and hexafluoroisopropanol, wherein the step of forming is devoid of any acid treatment, where the silk solution has a concentration of about 0.2 to about 1.5 weight percent silk in hexafluoroisopropanol, and where the silk is selected from *Bombyx mori* silk and *Nephila clavipes* silk; and electrospinning the solution, thereby forming a non-woven network of nanofibers having a diameter in the range from about 2 to about 2000 nanometers.

21 Claims, 6 Drawing Sheets

SYNTHETICALLY SPUN SILK NANOFIBERS AND A PROCESS FOR MAKING THE SAME

This application claims the benefit of U.S. Provisional Application No. 60/081,947 filed on Apr. 15, 1998 now abandoned.

TECHNICAL FIELD

The present invention is directed toward silk nanofibers. Specifically, the silk nanofibers are those obtained from *Bombyx mori, Nephila clavipes* or their synthetic equivalents. The nanofibers of the present invention are synthetically produced by electrospinning techniques. Accordingly, the present invention also provides a novel technique for obtaining silk nanofibers.

BACKGROUND OF THE INVENTION

Silk has been used as a textile material for over 4000 years. Due to its high (tensile) strength, luster, and ability to bind chemical dyes, silk remains the premier textile material in the world today.

Naturally occurring silk is produced by insects and spiders. Most commercially produced silk is harvested from cocoons of *Bombyx larva*, or silkworms (*B. mori* ). Unlike the silkworm, which produces silk only for use in building its cocoon, spiders produce a variety of different silks throughout their adult life. Although all spiders produce silk, the specialized use of silk is most developed in the orb-weaving spiders. The golden orb weaver spider, *Nephila clavipes* (*N. clavipes*), is one of the most carefully studied orb-weavers with respect to the production and properties of their silk. The orb-web weaving spiders produce a broad range of high-performance structural fibers with mechanical properties that are superbly matched to their function. These spiders produce seven different silks in various glands that are stored in the liquid state, and each is used to make silk for a specific purpose.

In particular, the Golden Orb Weaver spider constructs its dragline and its web frame threads using silk from the major ampullate gland. This so-called dragline silk has an unusual combination of high mechanical strength and elasticity because it must provide support for the web as well as allow significant web deformation without breaking when the spider's prey are caught. The strength and elasticity of the silk are also exhibited in its use as a dragline, which supports the spider's weight on a single thread and resists breaking when the spider falls. This desirable combination of strength and elasticity, as well as its other extraordinary mechanical properties, makes dragline silk a potentially useful commercial material.

Silk fiber in general exhibits mechanical properties similar or superior to other fibers. A few synthetic polymers such as Kevlar® have a slightly higher strength than *Nephila clavipes* dragline, but their toughness is significantly lower. The mechanical properties of dragline silk fibers are in general superior to those of *B. mori* silk fibers. The excellent mechanical properties of dragline silk indicate that it may be desirable to use in fiber-reinforced composite materials. Dragline silk fibers are stronger per unit weight than high-tensile steel and have tensile strength approaching that of aramid fibers. Dragline silk is exceptionally tough and can stretch to about one hundred and thirty percent, and absorb a tremendous amount of energy before failure.

Instead, the prior art teaches that polypeptides such as naturally occurring silkworm cocoon silk fiber can be dissolved under specific conditions followed by fiber spinning using any of several well-known methods. For example, U.S. Pat. No. 5,171,505 teaches the dissolution of natural or synthetic polypeptides in hexafluoropropanol or a formic acid/lithium halide mixture, followed by conventional wet, dry, or dry-jet wet spinning. Lock U.S. Pat. No. 5,252,285 teaches a method to spin fibers from cocoon silk. Noting that cocoon silk in its native fiber form is insoluble in hexafluoropropanol, Lock '285 teaches a pretreatment of dissolving cocoon silk in an aqueous salt solution, followed by dialysis to remove the salt and drying to remove the water; Lock '285 teaches that after this pretreatment, the cocoon silk is dissolved in hexafluoropropanol followed by fiber spinning by conventional wet, dry, or dry-jet wet spinning. Also, U.S. Pat. No. 5,252,277 teaches a method to spin polypeptides fibers from a solution of polypeptide in a liquified phenol and lithium thiocyanate.

A particular type of fiber reinforced composite material is the so-called nano composites. To be utilized as reinforcement in nanocomposites, fibers should be in the range of about 1 nm to about 1000 nm. Conventional techniques used to spin fibers from solution such as wet spinning, dry-jet wet spinning, and dry spinning produce fibers in the range of 10 to 100 microns. It is difficult to make nanometer-range diameter fibers using conventional spinning processes. In contrast, electrospinning is well suited to producing fibers with nanometer-range diameters. The diameter of electrospun fibers is typically one to two orders of magnitude smaller than the diameter of conventionally spun fibers. The use of electrospinning is well known in the art.

Another useful application for fibers in the nanometer size range is in materials characterization rising transmission electron microscopy (TEM) and electron diffraction (ED). Characterization of several physical properties of a material including but not limited to surface features and sample geometry (by Transmission electron microscopy) and crystalline content (by Electron diffraction) are facilitated using fibers in the size range of about 1 nm to about 5,000 nm.

Although the prior art teaches methods to produce fibers from polypeptides or silkworm silk, the prior art does not teach a method to spin nanofibers from spider dragline silk. Because dragline silk nanofibers are desirable as a reinforcement in nanocomposite materials as well as in other applications. A need exists, for a method to produce such fibers.

SUMMARY OF INVENTION

It is therefore, an object of the present invention to provide a silk nanofiber.

It is yet another object of the present invention to provide a method for producing a silk nanofiber.

It is still another object of the present invention to provide a silk nanofiber composite.

It is yet another object of the present invention to provide a method for producing a silk nanofiber composite.

It is another object of the present invention to provide a silk solution capable of being electrospun to form useful silk nanofibers and silk nanofiber composites.

At least one or more of the foregoing objects, together with the advantages thereof over the known art relating to silk fibers, which shall become apparent from the specification that follows, are accomplished by the invention as hereinafter described and claimed.

The present invention also includes a silk nanofiber produced by electrospinning a solution containing dissolved silk fibers.

In general the present invention provides a silk nanofiber composite network produced by forming a solution of silk fiber and hexafluroisopropanol, wherein the step of forming is devoid of any acid treatment, where the silk solution has a concentration of about 0.2 to about 1.5 weight percent silk in hexafluroisopropanol, and where the silk is selected from *Bombyx mori* silk and *Nephila clavipes* silk, and electrospinning the solution, thereby forming a non-woven network of nanofibers having a diameter in the range from about 2 to about 500 nanometers.

The present invention further includes a process for spinning polypeptide silk fibers comprising the steps of forming a solution comprising a polypeptide silk in hexafluroisopropanol, and electrospinning the solution, and thereby forming a silk fiber having a diameter having less than about 1 micrometer.

The present invention also includes a synthetically spun silk fiber comprising a silk fiber having a diameter in the range from about 8 to about 1,000 nanometers.

PREFERRED EMBODIMENT FOR CARRYING OUT THE INVENTION

Figure 1:
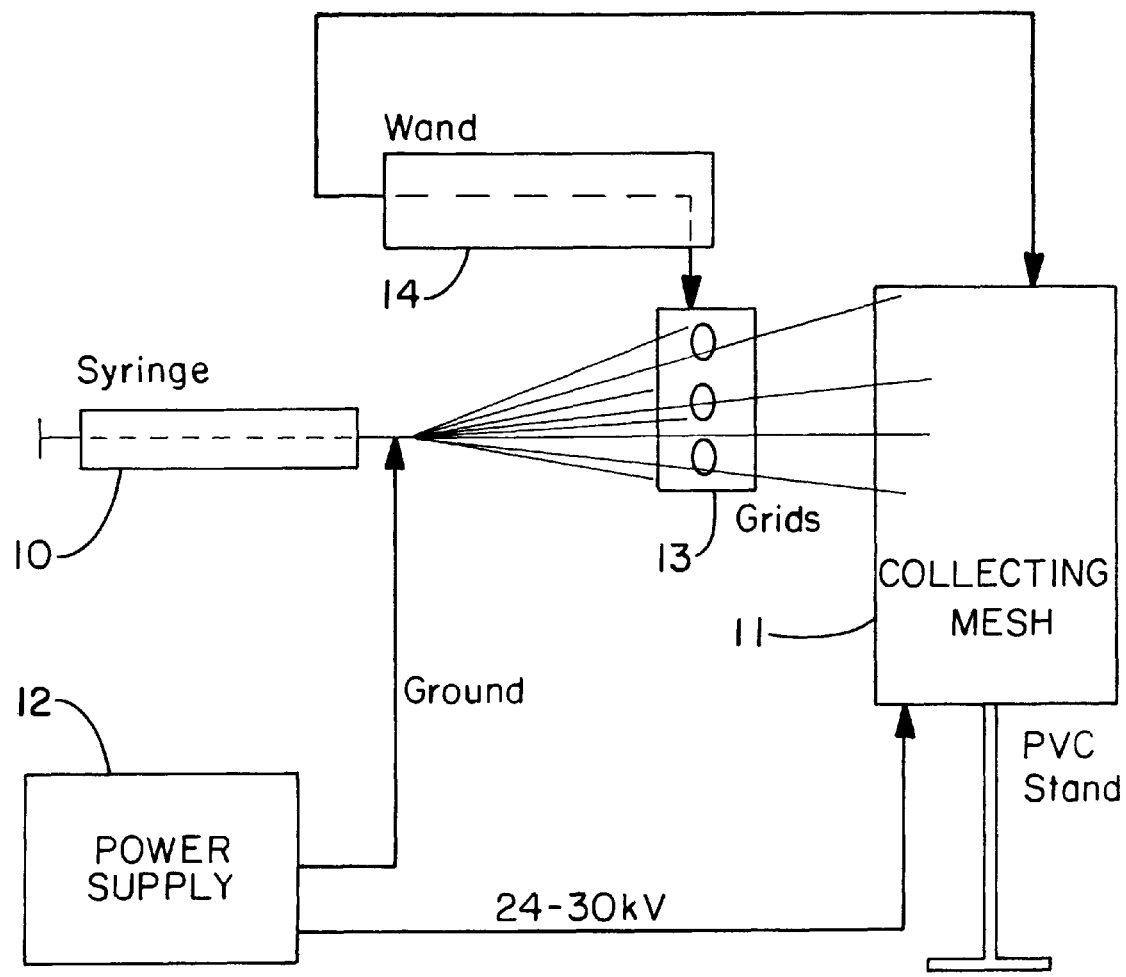
FIG. 1 depicts a preferred arrangement for electrospinning the silk fibers of the present invention; the figure showing various streams or jets of fiber resulting from the splaying phenomenon that can occur during electrospinning.

The present invention is directed toward synthetically spun silk nanofibers. Silk nanofilbers refere to those silk fibers that have been spun. In other words, these silk fibers are solid phase materials, and should be distinguished from liquid phase or gel state silk. The term synthetically spun refers to those fibers that are produced or spun by means, apparatus, or techniques other than by an animal, i.e., naturally spun fibers. An example of a naturally spun fiber is that produced by a spider.

As the skilled artisan will appreciate, a solid phase fiber is produced by drawing a viscous liquid or gel through a fine orifice. This liquid phase or gel can include native silk, which is an aqueous solution of silk polymer as found within the glands of animals. The liquid or gel can also include regenerated solutions of silk, which are obtained by dissolving naturally spun fibers within a solvent. Additionally, the liquid or gel can include genetically engineered silk-like solutions. An example of a genetically engineered silk-like solution is that disclosed by Prince et al., D. *Biochemistry*, Vol. 34 (1995), pp. 10879–10885 or Lewis et al. in *Protein Expression Purification*, Vol. 7 (1996), pp. 400–406.

It should be understood that the term silk, in general, refers to those numerous polypeptide high molecular weight polymers that are produced by a large variety of organisms. The term, of course, will also refer to those silk-like polymers that have been genetically engineered. Particularly useful silks include those produced by organisms within the phylum Arthropoda. Preferred Arthropoda include those species that fall within the classes Insecta and Arachnida, even more preferred are the species *Bombyx mori* and *Nephila clavipes*. Most preferred are the *Nephila clavipes* fibers obtained from the major ampullate gland, and the domestic *Bombyx mori*.

The nanofibers of the present invention have an average diameter of less than about 2,000 nanometers. Preferably, the average diameter of the fibers is from about 2 to about 2,000 nanometers, preferably from about 5 to about 1,000 nanometers, more preferably from about 8 to about 500 nanometers, and even more preferably from about 20 to about 200 nanometers, still more preferably from about 30 to about 120 nanometers, and most preferably from about 40 to about 80 nanometers. The skilled artisan will appreciate that the use of the term average diameter accounts for the fact that one single fiber strand may have a varying diameter across its length, and that the production of numerous fibers can produce fibers of different diameter.

In an especially preferred embodiment, nanofibers deriving from *Nephila clavipes* silk has an average diameter from about 5 to about 220 nanometers, with the majority of the fibers having an average diameter from about 90 to about 110 nanometers. In another preferred embodiment, where *Bombyx mori* silk is employed, the fibers have an average diameter from about 5 to about 120 nanometers, with the majority of the fibers having an average diameter from about 15 to about 30 nanometers. The skilled artisan will recognize that the average diameter of any fiber produced according to the present invention can be manipulated by altering or controlling the processing techniques that will be described hereinafter.

As for the geometry of the fiber, it is preferred that the fiber have a circular cross-section. Preferably, the surface of the fiber is smooth, which generally means that the surface irregularities on the surface of the fiber are less than 5 nanometers in depth, preferably less than 3 nanometers in depth, and even more preferably less than 1 nanometer in depth. Other useful geometries include ribbon-like structures and beaded structures. Also, although one embodiment of the present invention is directed toward single strands of nanofibers, other preferred embodiments include three dimensional networks of nanofibers, which may also be referred to as nanofiber composites. These three dimensional structures or networks are preferably non-woven sheets of a single fiber or multiple fibers. The fiber or fibers within the three dimensional networks of the present invention can have a similar geometry, or can have various geometries. A three dimensional network of nanofibers having various geometries is exemplified in FIG. 2.

The length of the fibers of the present invention is not critical, inasmuch as the fibers could be kilometers in length, or can be produced in the millimeter range. The skilled artisan will appreciate that fibers having a length in the millimeter range can be so sized by physically cutting the fibers.

According to the methods of the present invention, the silk nanofibers of the present invention are produced by electrospinning. As the skilled artisan will appreciate, the process of electrospinning creates a fine stream or jet of polymeric liquid that upon proper evaporation of a solvent will yield a nanofiber. The fine stream of liquid is produced by pulling a small amount of fiber solution through space by using electrical forces. The process of electrospinning has been described in "Electrospinning Process and Applications of Electrospun Fibers" by Doshi and Reneker, *Journal of Electrostatics,* Vol. 35 (1995), pp. 151–160, "Nanometer Diameter Fibres of Polymer, Produced by Electrospinning" by Reneker and Chun, *Nanotechnology,* Vol. 7 (1996), pp. 216–223, and "DNA Fibers by Electrospinning" by Fang and Reneker, *Journal of Macromolecular Science and Physics,* Vol. B36(2) (1997), pp. 169–173, which are hereby expressly incorporated by reference.

In general, the apparatus or setup needed to carry out the electrospinning of the present invention—and thereby produce the nanofibers of the present invention—includes a delivery point, which may include a delivery means, an electric field, and a capture point, which may include a capture or collection means.

The delivery point is simply a place where at least one droplet of silk solution can be introduced or exposed to an electric field. This delivery point can be oriented anywhere in space adjacent to the electric field; for example, the delivery point can be above the electric field, below the electric field, or horizontally adjacent to the electric field. The capture point is simply a place where the stream or jet of polymeric liquid can be collected. It is preferred that the delivery point and capture point be conductive so as to be useful in creating the electric field. But, it should be understood that the invention is not limited to this type of configuration or setup inasmuch as the delivery point and capture point can be non-conductive points that are simply placed within or adjacent to an electric field.

As for the electric field, the skilled artisan should appreciate that the electric field should be strong enough to overcome gravitational forces on the silk solution, overcome surface tension forces of the silk solution, provide enough force to form a stream or jet of solution in space, and accelerate that stream or jet across the electric field. As the skilled artisan will recognize, surface tension is a function of many variables. These variables include the type of polymer, the solution concentration, and the temperature.

Respecting the concentration of the silk solution, the concentration should be high enough so that randomly coiled polymeric molecules within the solution can come together and form an oriented array of molecules or a protofilament. At the upper extreme, the concentration should be lower than the saturation point of the silk. With this instruction, as well as the other teachings within this written description, the skilled artisan will be able to produce useful solutions that can be used to electrospin the nanofibers of the present invention. It should also be understood that it may be useful to electrospin within a vacuum environment because greater electrical forces can be used within the vacuum. These greater electrical forces may be needed to overcome greater forces associated with more concentrated solutions.

In a preferred embodiment, the electrospinning apparatus is configured so that the stream of fiber solution is pulled horizontally through space. This horizontal configuration is represented in FIG. 1, which includes delivery means 10, which is a syringe, collecting means 11, power supply 12 for generating an electric field, grids 13 for use with a transmission electron microscope, and wand 14, which is a mobile collecting means for gathering fibers. As noted above, the technique employed in electrospinning the silk fibers of the present invention need not employ a delivery means that horizontally delivers fluid to the electric field. It has, however, been found to be particularly useful to employ this configuration because the horizontal delivery configuration can be used in conjunction with a pumping means that allows the solution to be pumped to the tip of the delivery means at a constant volume rate so that skins that are sometimes found on the surface of the solution are continuously broken as the solution is delivered to the electric field. It should be appreciated that the dripping of the solution from the delivery means should be avoided. To do so, the pressure at the orifice of the delivery means should be less than that associated with the surface tension of the solution. The skilled artisan will appreciate that there are other ways by which one could control the delivery of the silk solution of the electric field. Other techniques include manipulating the size of the orifice of the delivery means, or manipulating the air pressure above the solution within the delivery means.

Accordingly, the fiber solution is introduced to the electrified field via a delivery device or means for delivering the fiber solution to the electrified field. These devices or means should include an orifice that is capable of delivering a controlled amount of fiber to the field. The preferred orifice should have a diameter from about 0.5 to about 1.0 mm. As noted above, it is preferred that the fiber solution be delivered to the electrified field horizontally so that gravitational forces do not introduce an excess amount of liquid into the electrified field. In one example, fiber solution is delivered to an electrified field via a horizontally mounted syringe. In another example, a pipet containing a conductive portion, such as a wire, can be used. The skilled artisan will be able to readily select other devices or means that can deliver a controlled amount of fiber solution to the electrified field. As noted above, a delivery means is not necessary for carrying out the electrospinning process of the present invention inasmuch as silk fibers can be spun from a simple droplet of silk solution. Also, electrospinning can be carried out from a beaker of solution, from a watch glass of solution, or even from one's hand.

Preferably, the stream of fiber solution is delivered to a collecting or capturing device, or means for capturing the stream of fiber solution. Non-limiting examples of a capturing device or means for capturing include a wire mesh, a polymeric mesh, or a water bath. The skilled artisan will be able to readily select other devices or means that can be employed to capture the fiber solution as it travels through the electric field. Typically, the collecting or capturing device is conductive, but need not be conductive inasmuch as a non-conductive capturing device can be employed in conjunction with a conductive material such as a foil.

As the skilled artisan will recognize, the electrified field necessary to create a stream of fiber solution through space can be achieved by charging the delivery means or the capture means. Where the delivery means is charged, the capture means will be grounded; and where the capture means is charged, the delivery means will be grounded.

In one embodiment, a solution of from about 0.2 to about 1.3 weight percent of *Nephila clavipes* within hexafluroisopropanol, at room temperature and pressure, typically requires an electric field of about 24 to about 30 kV, and the distance between the delivery means and the capture means is from about 10 to about 15 centimeters cm. In another embodiment, a solution of from about 0.6 to about 0.8 weight percent of *Bombyx mori* within hexafluroisopropanol, at room temperature and pressure, typically requires an electric field of from about 24 to about 30 kV, and a distance between the delivery means and the capture means of about 10 to about 15 cm. The spinning rate is controlled by adjusting both the flow of the fiber solution and the electric field.

Because the process of electrospinning creates a fine stream of polymeric solution, the fibers being electrospun must be placed into solution. By placed into solution, it should be understood that the silk fibers are not digested. In other words, the solvent employed should not deleteriously impact the chemical makeup of the fiber. It is believed that solvents that do not digest the polymeric structure of the fiber and yet form liquid solutions of the polymer do so by impacting the crystalline structure of the polymer or fiber. In other words, the distinction between dissolving a polymer fiber and digesting the fiber is that when a polymer is dissolved it only undergoes a phase transition from solid to liquid. The backbone remains intact and there is no significant change in the molecular weight.

In addition to placing the fibers into solution, a solvent be selected that will not deleteriously impact the electrospinning process. Namely, the solvent selected should sufficiently evaporate from the fiber without leaving a residue that will deleteriously impact the physical properties of the resulting fiber. It has surprisingly been found that hexafluroisopropanol will sufficiently dissolve both *B. mori* and *Nephila clavipes* fibers, will not interfere with the electrospinning process, and allow for the formation of silk fibers of unexpectedly high quality. Advantageously, *Nephila clavipes* fibers are readily dissolved in hexafluroisopropanol without any pretreatment from a chemical such as lithium bromide or other salt or acid. *Bombyx mori* fibers are likewise dissolved over a longer period of time. Accordingly, in preparing a spinnable solution of *Nephila clavipes* fiber according to the present invention, useful solvents include hexafluroisopropanol, such as 1,1,1,3,3,3-hexafluroisopropanol, and hexafluro-2-propanol. Hexafluroisopropanol is readily available from a number of vendors including Aldrich Chemical.

It has been specifically found that the *B. mori* fibers are dissolved in hexafluroisopropanol over an extended period of time, such as five months, while *Nephila clavipes* fibers have been found to be immediately soluble in hexafluroisopropanol. By immediately soluble, it is meant that the fiber will enter the liquid state or go into solution within twenty minutes. The duration of time in which the *B. mori* fibers are dissolved within hexafluroisopropanol can be shortened with mechanical manipulation of the fibers, including physically shortening the fibers by cutting or chopping.

Respecting the silk solution, where natural silk fibers obtained from the major ampullate of the *Nephila clavipes* is employed, a preferred solution is prepared that contains from about 0.2 to about 1.5 percent by weight of silk in hexafluroisopropanol. More preferably, the solution will contain from about 0.5 to about 1.3 percent by weight of silk in hexafluroisopropanol, and even more preferably from about 0.8 to about 1.2 percent by weight of silk in hexafluroisopropanol. As noted above, the major ampullate *Nephila clavipes* fiber readily dissolves in hexafluroisopropanol at room temperature.

In another embodiment, where natural silk fibers obtained from *Bombyx mori* are employed, a preferred solution contains from about 0.5 to about 1.2 percent by weight of silk in hexafluroisopropanol. More preferably, the solution will contain from about 0.6 to about 1.0 percent by weight of silk and hexafluroisopropanol, and even more preferably from about 0.7 to about 0.8 percent by weight of silk in hexafluroisopropanol.

Once the nanofibers of the present invention have been electrospun and collected, it has been found to be particularly useful for the fibers to be annealed. For *Nephila clavipes* fibers, annealing is preferably accomplished at a temperature of about 50° C. to about 280° C., and more preferably at a temperature of about 210° C. to about 225° C. For *Bombyx mori* fibers, annealing is preferably accomplished at a temperature of about 150° C. to about 300° C., and more preferably at a temperature of about 205° C. to about 245° C. When annealing is conducted at the above preferred temperature ranges, useful crystalline diffraction patterns can advantageously be achieved. The annealing process should be conducted for a period of about 0.5 to about 1.0 hours.

The silk nanofibers of the present invention have been found to be particularly advantageous because of the relatively small fiber diameter that can be achieved. In fact, the diameter of the electrospun *Nephila clavipes* fibers are at least one order of magnitude smaller than the naturally spun fibers, and the electrospun *Bombyx mori* fibers are at least three orders of magnitude smaller than the naturally spun fibers. Because of this diameter, the silk fibers can be used to form nano composites, including novel filtration devices, and can be used in biomechanical applications where nanofibers are required. Another advantage of producing fibers having a diameter of less than about 1 micrometer is the ability to analyze the fiber for many of its physical and chemical characteristics.

In order to demonstrate the practice of the present invention, the following examples have been prepared and tested as described in the General Experimentation Section disclosed hereinbelow. The examples should not, however, be viewed as limiting the scope of the invention. The claims will serve to define the invention.

GENERAL EXPERIMENTATION

Examples 1–7 hereinbelow demonstrate the practice of the present invention. Examples 8–12 are provided as comparative examples to demonstrate the superiority of the present invention.

EXAMPLE 1

Preparation of Dragline Silk Solution

Samples of *Nephila clavipes* dragline silk were place in sterile glass bottles and hexafluroisopropanol was added to a final concentration of about 0.23 to about 1.2 weight percent of silk. The bottle was sealed shut to prevent solvent evaporation. Rapid dissolution was observed within 20 minutes at room temperature. The solution was used immediately for electrospinning, and also remained stable as it was used for spinning successfully a few months later. The electrospinning of the solution is explained below.

EXAMPLE 2

Preparation of *B. mori* Silk Solution

Degummed cocoon silk from *B. mori* was cut into lengths of a few millimeters and placed in a sterile glass bottle. Hexafluroisopropanol was added to a final concentration of 0.74 weight percent of silk. No visible dissolution was observed at room temperature. The bottle was sealed shut and set aside. The *B. mori* fibers eventually dissolved after a period of up to about five months at room temperature. The solution was used for electrospinning as described below.

EXAMPLE 3

Electrospinning of Silk Solutions

The silk solutions from Examples 1 and 2 were individually placed in a Hamilton 25 microliter syringe driven by a compact infusion pump (Model No. 975, Harvard Apparatus Co. Inc, Denver, Mass.). A metal receiving mesh was placed at a distance of about 15 cm from and perpendicular to the syringe tip. A 30 kV charge was supplied to the receiving mesh by a high voltage power supply, while the tip of the syringe was grounded. The spinning process was carried out at room temperature, and the spinning rate was controlled by adjusting the flow of the silk solution and the electrical field. Electrospinning of each solution produced a non-woven sheet of randomly arranged nano-scale *Nephila clavipes* and *B. mori* silk fibers.

EXAMPLE 4

SEM of Electrospun Silk Fibers

Figure 2:
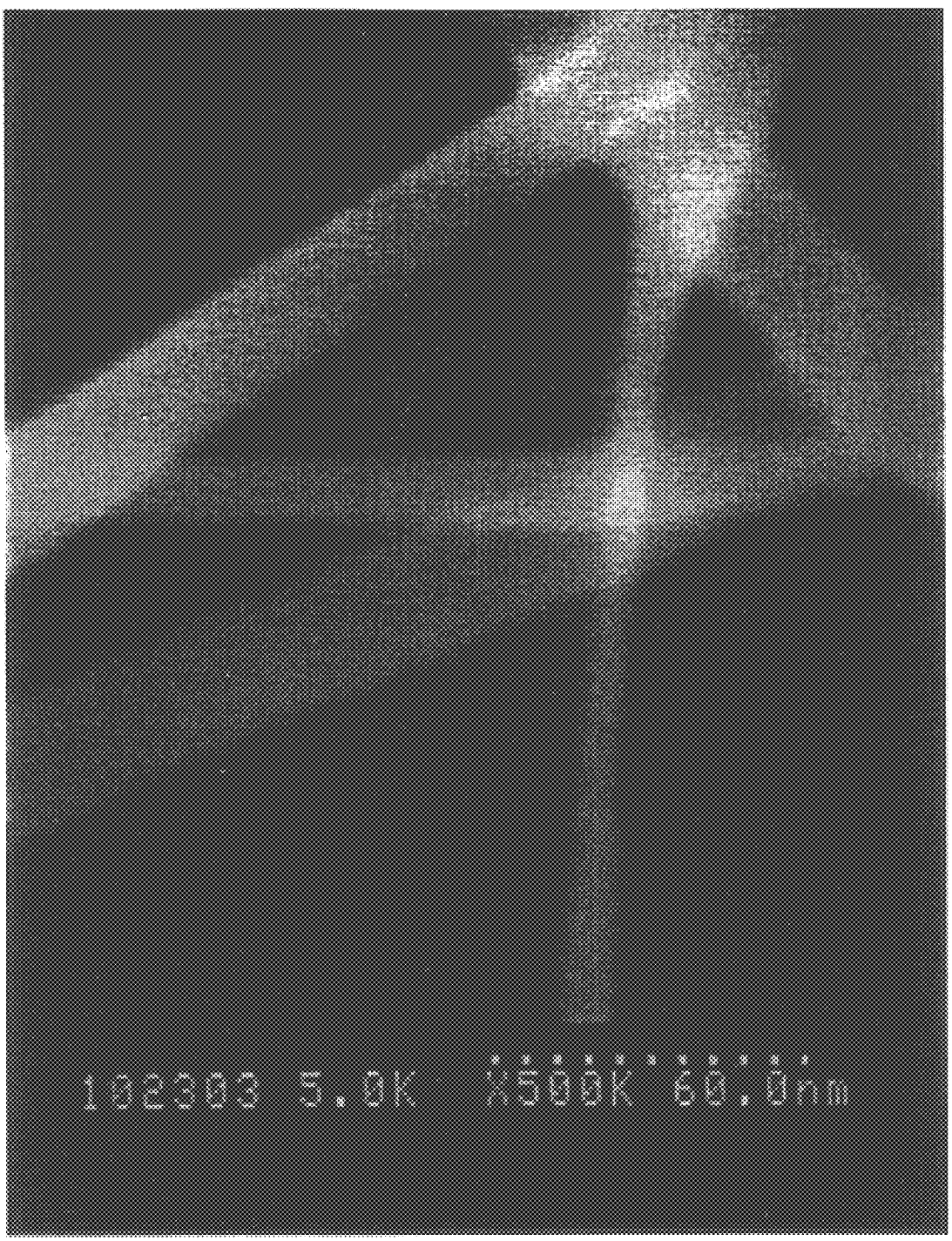
FIG. 2 depicts a non-woven silk fiber network produced by electrospinning a *Bombyx mori* silk solution according to the present invention as observed through a scanning electron microscope at 5 kV.
Figure 3:
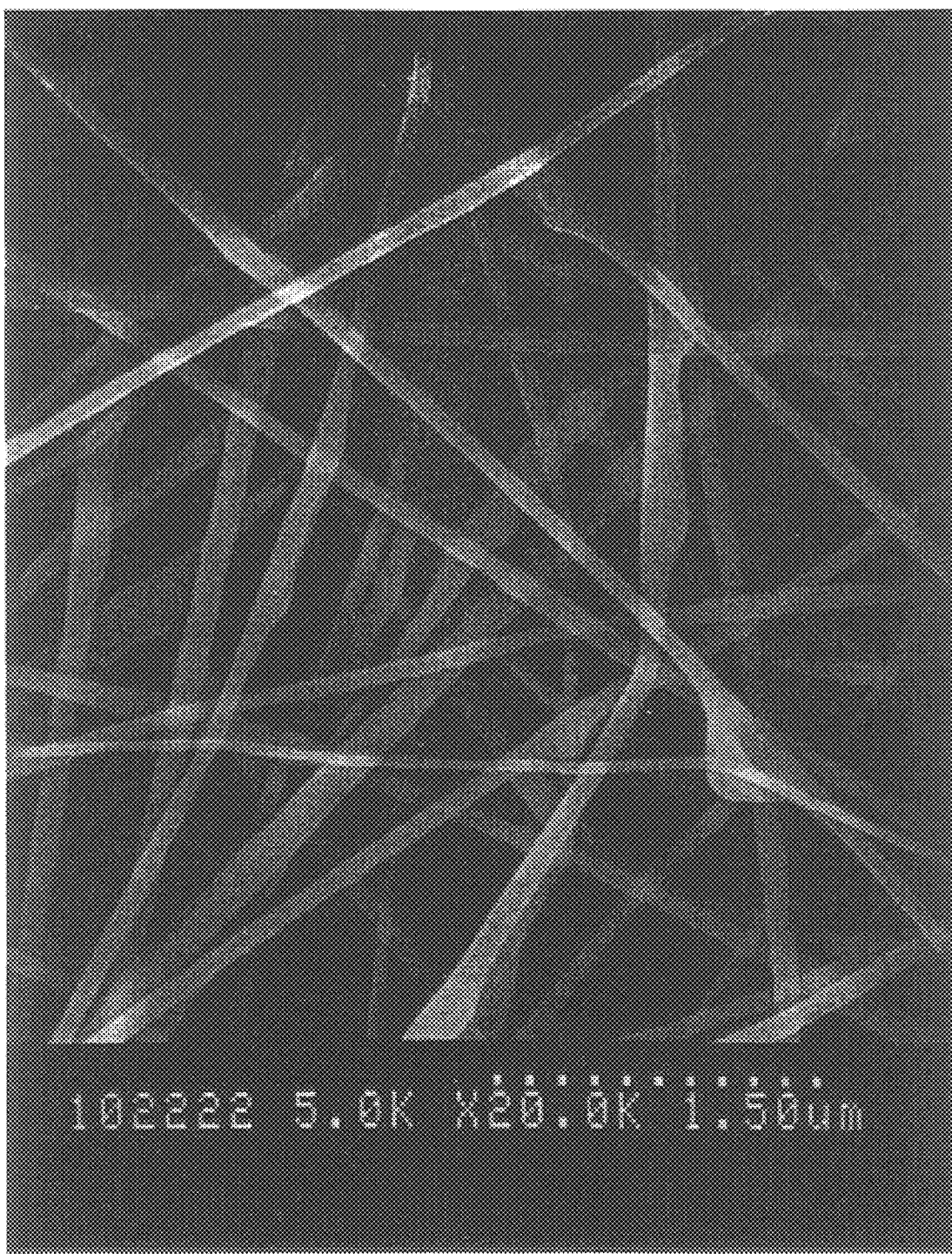
FIG. 3 depicts *Bombyx mori* silk fibers produced by electrospinning according to the present invention as observed through a scanning electron microscope at 5 kV.
Figure 4:
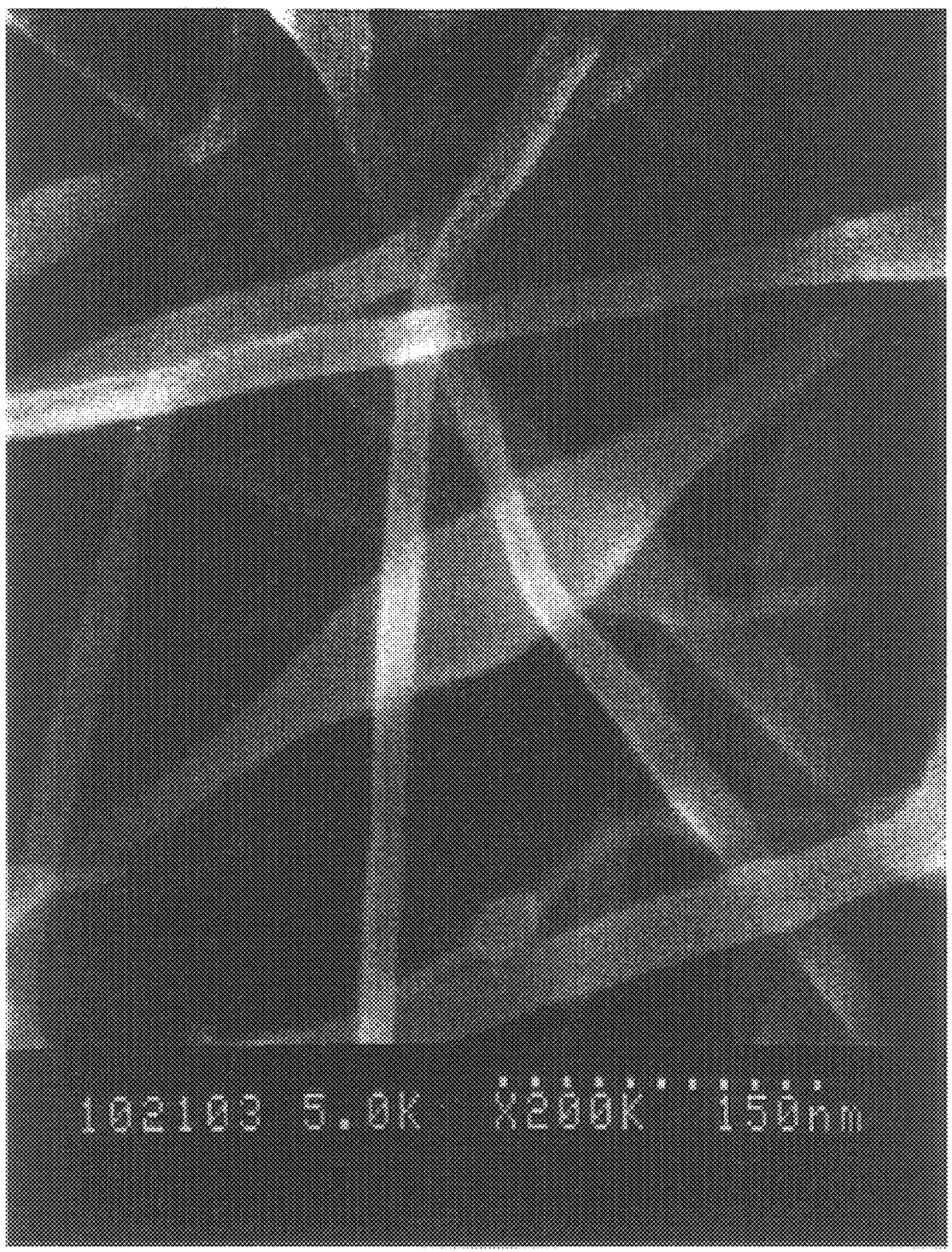
FIG. 4 depicts a non-woven silk fiber network produced by electrospinning *Nephila clavipes* silk according to the present invention as observed through a scanning electron microscope at 5 kV.

Fibers produced using the method of Example 3 generally showed a circular cross section and a smooth surface with no deleterious surface features when observed at high magnifications with a low voltage scanning electron microscope. The fiber diameters ranged from 8 nm to 206 nm. The *Bombyx mori* nanofibers are shown in FIGS. 2 and 3, and the *Nephila clavipes* nanofibers are shown in FIG. 4.

EXAMPLE 5

Annealing of Silk Nanofibers

Silk fibers produced using the method of Example 3 were annealed at a temperature ranging from about 50° C. to about 300° C. for about 1 hour. Crystalline diffraction was observed to occur in *Nephila clavipes* fibers in the range of about 210° C. to about 225° C., and was observed in *Bombyx mori* fibers in the range of about 205° C. to about 245° C.

EXAMPLE 6

Electron Diffraction of *B. mori* Electrospun Fibers *Bombyx mori* silk fibers electrospun from the solution of Example 2, using the method of Example 3, were characterized using electron diffraction. The *B. mori* electrospun fibers produced two equatorial reflections corresponding to that of the naturally spun fibers.

EXAMPLE 7

Electron Diffraction of *N. clavipes* Electrospun Fibers

*Nephila clavipes* silk fibers electrospun from the solution of Example 1, using the method of Example 3, were characterized using electron diffraction. The *N. clavipes* electrospun fibers produced three equatorial reflections corresponding that of the naturally spun fibers.

EXAMPLE 8

In a comparative test, 7 milligrams of *Nephila clavipes* dragline silk were placed into a sterile glass bottle with 2 milliliters of 6 M hydrochloric acid as a solvent. The fibers dissolved at room temperature. A droplet of this polymer solution was placed on a glass slide to test its ability to form fibers. The polymer droplet was rapidly drawn across the glass slide with a sharp tweezer tip and/or rod-like structure. This mechanical test was used as a screening technique because solutions that cannot be employed to mechanically draw fibers will most likely not be useful for electrospinning. The fiber solution of this example was unable to form a mechanically drawn fiber. It is believed that the acid led to the degradation of the fiber. No further effort was made to spin the solution.

EXAMPLE 9

In another comparative test, 7 milligrams of *Nephila clavipes* dragline silk were placed into a sterile glass bottle with an 88 percent solution of 2 milliliters of formic acid as a solute. The fibers dissolved at room temperature. A droplet of this polymer solution was placed on a glass slide to test its ability to form fibers. The polymer droplet was rapidly drawn across the glass slide with a sharp tweezer tip. The fiber solution of this example was able to form a mechanically drawn fiber. But, this solution was not useful for electrospinning. It is believed that the acidic solution led to the eventual degradation of the fiber. No further effort was made to spin the solution.

EXAMPLE 10

In still another comparative test, 7 milligrams of *Nephila clavipes* dragline silk were placed in sterile glass bottles with 2 milliliters of 9 M lithium bromide as a solvent. The fibers dissolved at room temperature. The solution was filtered using a Whatman® Anodisc 47, 0.02 μm filter, which is available from Whatman International, Ltd. A droplet of this polymer was mechanically drawn by using the technique discussed above. The filtered solution was then poured into a dialysis membrane. Dialysis was carried out, against deionized water, at room temperature and steady stirring for three days. This resulted in unoriented micron sized regenerated fibers. This silk solution could not be electrospun.

EXAMPLE 11

Figure 5:
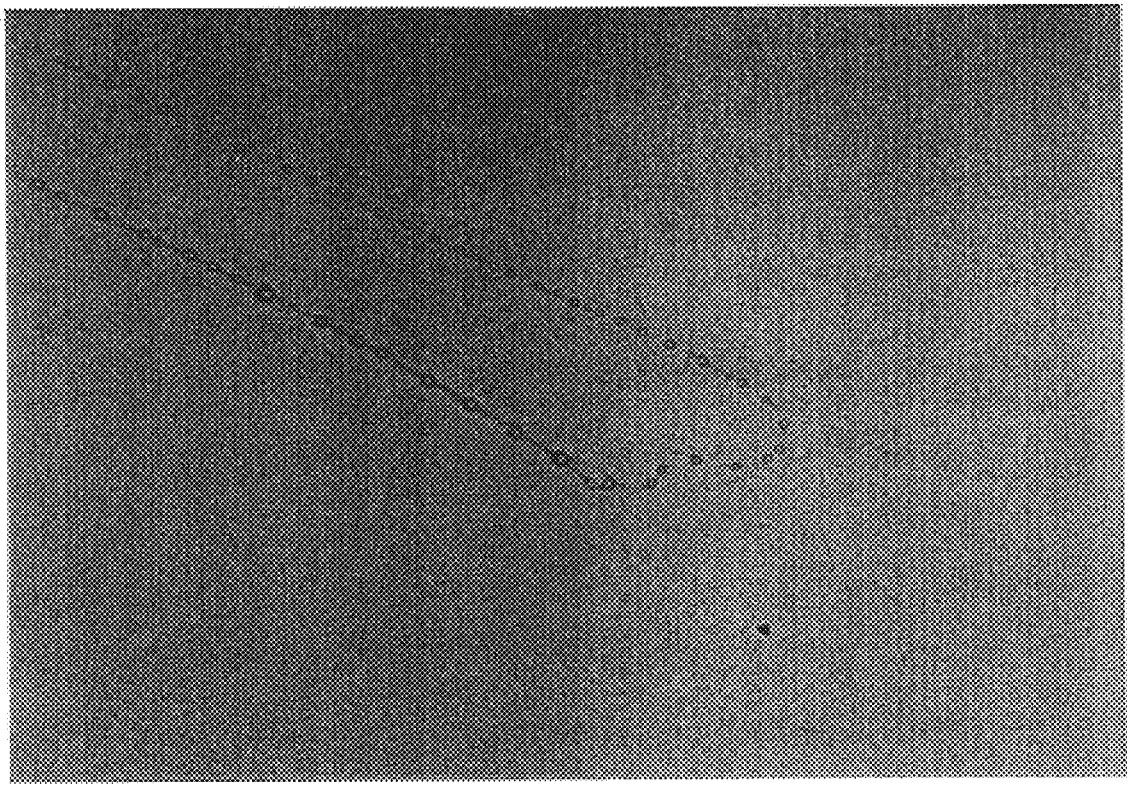
FIG. 5 depicts a mechanically drawn *Nephila clavipes* fiber produced from a solution of silk in calcium nitrate and methanol as observed through an optical microscope.

In yet another comparative test, 7 milligrams of *Nephila clavipes* dragline silk were placed in sterile glass bottles with 2 milliliters of a 75 percent solution of calcium nitrate in methanol as a solvent. The fibers were dissolved at room temperature. A droplet of this polymer solution was placed on a glass slide to test its ability to form mechanically drawn fibers as set forth above. Mechanically drawn fibers were obtained, and using an optical microscope were determined to have a diameter of about 30 μm. A fiber from this example is shown in FIG. 5. The mechanically drawn fibers, however, were hygroscopic and remained wet.

EXAMPLE 12

Figure 6:
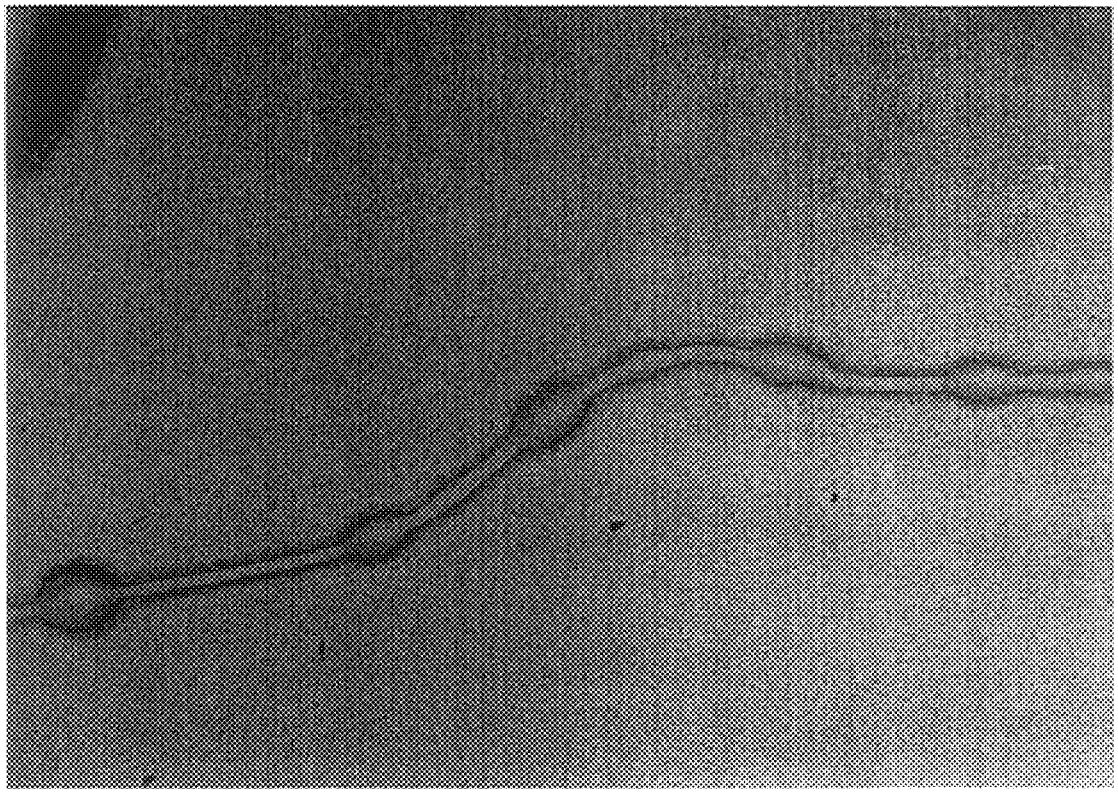
FIG. 6 depicts a *Nephila clavipes* electrospun fiber as produced from a solution of silk in calcium nitrate and methanol as observed through an optical microscope.

The fiber solution formed in Example 11 was used for electrospinning in a similar fashion to that described above. The electrospun fibers were collected on a glass slide and observed by an optical microscope. A fiber from this example is shown in FIG. 6. These fibers had an average diameter of 10 μm. The resulting fibers were, however, hygroscopic and remained wet. The fibers were, therefore, not useful for performing Transmission electron microscopy or Electron diffraction.

Additional experimental data and explanation is contain in the Doctoral Thesis of Shahrzad Zarkoob, University of Akron, 1998, the entire contents of which are hereby incorporated by reference. Also, reference can be made to "Structure and Morphology of Nano Electrospun Silk Fibers," Zarkoob et. Al., 1998, which is also hereby expressly incorporated by reference.

Based upon the foregoing disclosure, it should now be apparent that the silk nanofibers, and the processes for preparing the same, as described herein, will carry out the objects set forth hereinabove. It is, therefore, to be understood, that any variations evident fall within the scope of the claimed invention, and thus, the selection of other silk fibers that can be electrospun can be selected without departing from the spirit of the invention herein disclosed and described. Moreover, as noted hereinabove, other electrospinning configurations, including other means for delivering a silk solution to an electrified field or capturing the silk nanofibers from the electrified field can be substituted for those described herein. Thus, the scope of the invention shall include all modifications and variations that may fall within the scope of the attached claims.

What is claimed is:

1. A non-woven network of synthetically-spun silk nanofibers produced by the process comprising the steps of:

forming a solution of silk and hexafluroisopropanol, wherein said step of forming is devoid of any acid treatment, where the silk solution has a concentration of about 0.2 to about 1.5 weight percent silk in hexafluroisopropanol, and where said silk is selected from *Bombyx mori* silk and *Nephila clavipes* silk; and elctrospinning the solution, thereby forming a non-woven network of nanofibers having a diameter in the range of about 2 to about 2000 nanometers.

2. A network of synthetically-spun silk nanofibers produced by the process comprising:

forming a solution of silk and solvent, where the silk solution has a concentration of about 0.2 to about 1.5 weight percent silk in the solvent; and electrospinning the solution, thereby forming a non-woven network of nanofibers having a diameter in the range of about 30 to about 2000 nanometers.

3. A network of synthetically-spun silk nanofibers produced by the process comprising:

forming a solution of silk and solvent, wherein said step of forming is devoid of any acid treatment, where the silk solution has a concentration of about 0.2 to about 1.5 weight percent silk in solvent, and where said silk is selected from *Bombyx mori* silk and *Nephila clavipes* silk; and elctrospinning the solution, thereby forming a non-woven network of nanofibers consisting essentially of *Bombyx mori* silk or *Nephila clavipes* silk having a molecular weight significantly similar to the molecular weight of naturally occurring *Bombyx mori* silk and *Nephila clavipes* silk.

4. A network of claim 1, wherein said silk nanofibers are electrospun from a solution containing dissolved *Nephila clavipes* silk.

5. A network of claim 1, wherein said silk nanofibers are electrospun from a solution containing dissolved *Bombyx mori* silk.

6. A network of claim 4, wherein said *Nephila clavipes* silk is major ampullate silk.

7. A network of claim 2, wherein said silk nanofibers are electrospun from a solution containing dissolved *Nephila clavipes* silk.

8. A network of claim 2, wherein said silk nanofibers are electrospun from a solution containing dissolved *Bombyx mori* silk.

9. A network of claim 7, wherein said *Nephila clavipes* silk is major ampullate silk.

10. A network of claim 1, wherein said method of electrospinning includes horizontally drawing a stream of said silk solution though an electrified field.

11. A network of claim 2, wherein said method of electrospinning includes horizontally drawing a stream of said silk solution though an electrified field.

12. A network of claim 3, wherein said method of electrospinning includes horizontally drawing a stream of said silk solution though an electrified field.

13. A network of claim 1, wherein said solution contains between about 0.5 and about 1.3 percent by weight *Nephila clavipes* silk.

14. A network of claim 1, wherein said solution contains between about 0.8 and about 1.2 percent by weight *Nephila clavipes* silk.

15. A network of claim 1, wherein said solution contains between about 0.5 and about 1.2 percent by weight *Bombyx mori* silk.

16. A network of claim 1, wherein said solution contains between about 0.7 and about 0.8 percent by weight *Bombyx mori* fiber.

17. A network of claim 1, wherein the diameter of the nanofibers is in the range of about 20 to 200 nanometers.

18. A network of claim 3, wherein the diameter of the nanofibers is in the range of about 20 to 200 nanometers.

19. A network of claim 2, wherein the diameter of the nanofibers is in the range of about 40 to 80 nanometers.

20. A network of claim 4, wherein the diameter of the nanofiber is at least one order of magnitude smaller than naturally produced *Nephila clavipes* fiber.

21. A network of claim 5, wherein the diameter of the nanofiber is at least three orders of magnitude smaller than naturally produced *Bombyx mori* fiber.

* * * * *